United States Patent [19]
Zamba

[11] Patent Number: 5,800,427
[45] Date of Patent: Sep. 1, 1998

[54] ELECTRO-SURGICAL BLADE

[76] Inventor: Gene Zamba, c/o BioGenetic Technologies, Inc., 13620 Wright Cir., Tampa, Fla. 34626

[21] Appl. No.: 773,955

[22] Filed: Dec. 26, 1996

[51] Int. Cl.$^6$ .................................................. A61B 17/36
[52] U.S. Cl. ....................................... 606/39; 606/40
[58] Field of Search ......................... 606/32, 37, 39, 606/41, 45, 167, 33

[56] References Cited

U.S. PATENT DOCUMENTS

| | | |
|---|---|---|
| 3,938,527 | 2/1976 | Rioux et al. . |
| 4,314,559 | 2/1982 | Allen .................................. 606/45 |
| 4,548,207 | 10/1985 | Reimels . |
| 4,706,667 | 11/1987 | Roos . |
| 4,754,754 | 7/1988 | Garito et al. ........................ 606/45 |
| 4,802,476 | 2/1989 | Noerenberg et al. . |
| 4,869,259 | 9/1989 | Elkins . |
| 4,924,882 | 5/1990 | Donovan . |
| 4,977,897 | 12/1990 | Hurwitz . |
| 5,100,402 | 3/1992 | Fan . |
| 5,197,962 | 3/1993 | Sansom et al. ...................... 606/45 |
| 5,374,188 | 12/1994 | Frank et al. . |
| 5,380,320 | 1/1995 | Morris ................................ 606/45 |
| 5,490,521 | 2/1996 | Davis et al. . |

OTHER PUBLICATIONS

U.S. Patent 4,785,807, filed Nov. 22, 1988 (abstract only).

*Primary Examiner*—Gary Jackson
*Assistant Examiner*—William Lewis
*Attorney, Agent, or Firm*—Spencer & Frank

[57] ABSTRACT

The present invention is a device and method for making electro-surgical devices, such as electro-surgical blades, that have a thin coating of non-stick material with a narrow continuous gap, or stretch of opening, in the coating, exposing the metal surface along an edge. This opening has a shape that tends to prevent it being clogged by charred tissue in use. The present invention includes a method of manufacturing the devices that has fewer steps than the prior art, and a better way of forming an opening in the electrically insulating non-stick coating to electrically expose the metal beneath.

9 Claims, 1 Drawing Sheet

ELECTRO-SURGICAL BLADE

BACKGROUND OF THE INVENTION

1. Field of the Invention

This invention relates to electro-surgical devices and methods of manufacturing them. More specifically, the invention involves electro-surgical blades and other electro-surgical devices that are coated with a non-stick coating, which coating has insulating properties regarding electricity.

2. Related Art

Electro-surgical devices are well known, including cauteries, surgical pencils, blades, loops, balls, tips and other shapes. Furthermore, it is known to coat electro-surgical blades and other electro-surgical devices with a non-stick fluorocarbon such as Teflon. The entirely uncoated prior art electro-surgical tip device discharges electricity that cuts the tissue with such electrical discharge, rather than with a sharp edge. However, the burning effect from the electricity tends to cause burnt tissue to stick to the electro-surgical tip, thus causing it to be dirty and misdirecting the electrical discharge because of the insulated effect to electricity of the charred tissue sticking to the device. The non-stick coating tends to prevent the charred tissue from sticking to the device. However, the non-stick coatings in themselves have an insulation effect regarding electricity, and this effect complicates the flow of electricity from the blade or other device to the tissue.

Some prior art uses perforated holes through the non-stick coating, leaving bare spots on the underlying metal blade. This provides a directed outlet for the electric current through the holes in the coating. However, the small holes tend to become clogged with charred tissue, sealing off the electro-conductive effect.

It is known in the prior art, U.S. Pat. No. 4,785,807, to entirely coat an electro-surgical blade with a non-conductive coating. This total coating may tend to minimize sticking of charred tissue to the device, since there are no holes in the coating. The coating is applied so that electricity can pass through the coating, if adequate increased current is used. Problems with this device arise because of the additional current that is required. Specifically, there are difficulties in accurately directing the path that the electricity uses from the blade through the coating to the tissue, since there is no particular path of least resistance through the coating.

SUMMARY OF THE INVENTION

The present invention is a device and method for making electro-surgical devices, such as electro-surgical blades, that have a thin coating of non-stick material with a narrow continuous gap, or stretch of opening, in the coating, exposing the metal surface. This opening has a shape that tends to prevent it being clogged by charred tissue in use. The present invention includes a method of manufacturing the devices that has fewer steps than the prior art, and a better way of forming an opening in the electrically insulating non-stick coating to electrically expose the metal beneath.

It is an object of the present invention to provide a superior electro-surgical device such as electro-surgical blades, that are mostly coated with a non-stick coating, but have small exposed areas of the underlying metal blade to direct the flow of electricity, but such exposed areas have such shapes that they tend not to clog in use.

It is an object of the present invention to provide a safer non-stick electro-surgical tip, using a lower electrical charge.

A further object of the present invention is to provide a cheaper simpler and superior method of applying the non-stick coating, so that better performing exposed areas are formed.

Further objectives and advantages will become apparent from a consideration of the description and drawings.

BRIEF DESCRIPTION OF THE DRAWINGS

The invention is better understood by reading the following detailed description with reference to the accompanying figure.

DETAILED DESCRIPTION OF THE PREFERRED EMBODIMENTS

Figure 1:
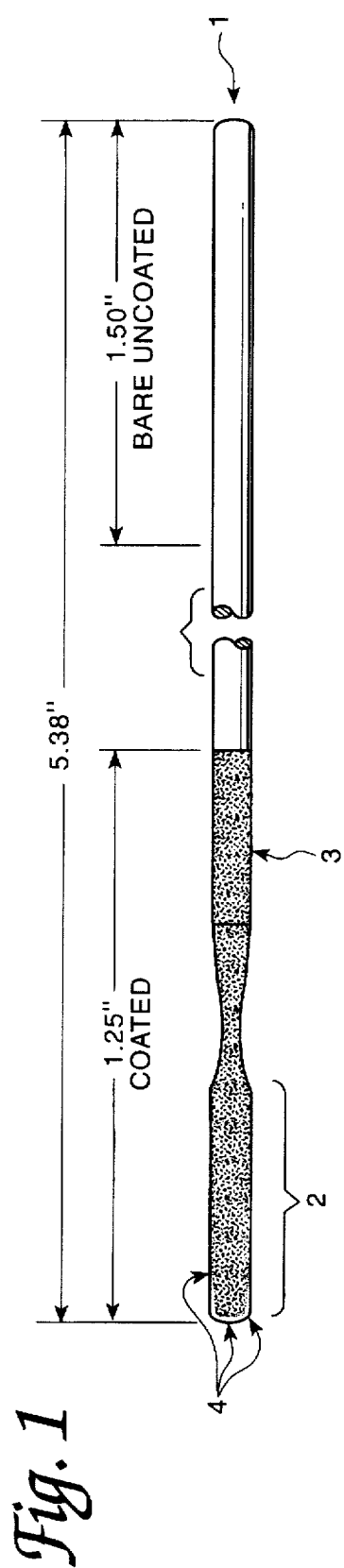
FIG. 1 shows an electro-surgical blade with the coating of the present invention.
Figure 2:
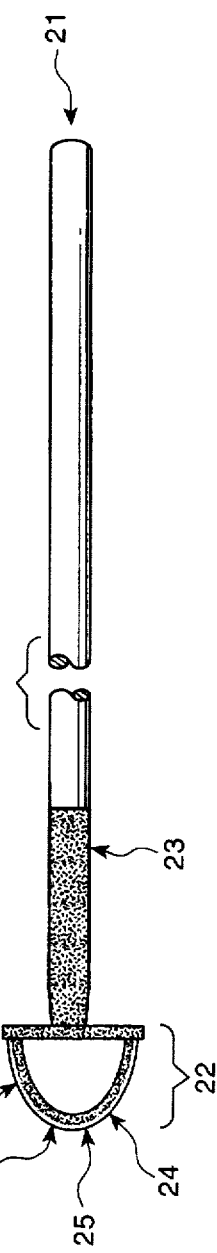
FIG. 2 shows the present invention with a loop shape tip portion.
Figure 3:
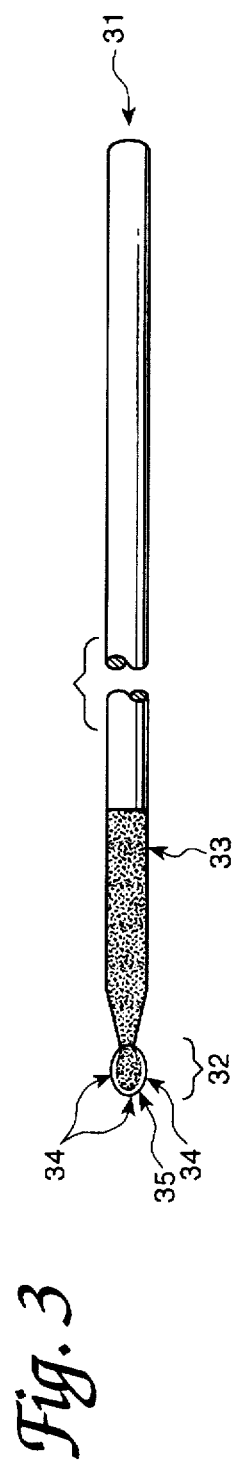
FIG. 3 shows the present invention with a ball shape tip portion.

In describing preferred embodiments of the present invention illustrated in the drawings, specific terminology is employed for the sake of clarity. However, the invention is not intended to be limited to the specific terminology so selected, and it is to be understood that each specific element includes all technical equivalents which operate in a similar manner to accomplish a similar purpose.

FIG. 1 shows an electro-surgical tip device embodiment of the present invention. The shank 1 of the device ends at the blade 2 of the device, which is more or less flat. The coating 3 covers blade 2 and any portion of shank 1 adjacent to blade 2. The edge 4 of blade 2 is exposed by a continuous break in the surface of the non-stick coating 3 at edge 4. The gap or break may be from about 2 to about 5 microns wide, and is not shown because of its small size. The dimensions of the parts of the device and the gap may vary depending on the particular application. In a preferred embodiment, the length of the bare uncoated portion of the shank is at least about 1.5 inches, the length of the coated portion of the blade at least about 1.25 inches, and the overall length of the device is about 5.38 inches.

A preferred embodiment of the present invention has no need for a pre-coat of primer applied to the metal surface prior to applying the non-stick coating, as found in the prior art in U.S. Pat. No. 4,785,807 and elsewhere.

In a preferred embodiment of the present invention, the surface of the metal of the blade or other electro-surgical tip is roughened to give a non-shiny texture to the metal surface that allows the non-stick coating to properly adhere to the metal without a pre-coat of primer. The roughening can be accomplished by any method known to one of ordinary skill in the art. For example, the surface may be airblasted with tiny glass particles, or rough tumbled with cutting compound such as #108 for a suitable period, such as 45 minutes. The metal part is then heated to allow oxidation of the metal surface which further prepares the metal surface to adhere to the non-stick coating without need for a primer coat. Heating may be to about 800° F. in an air environment at about one atmosphere pressure for about 30 minutes. Higher or lower temperatures, pressures, or lengths of time may be suitable to prepare the metal surface as can readily be determined by a person of ordinary skill.

The prepared metal tip is then dipped in a liquid solution of the coating material and dried. In a preferred embodiment the non-stick coating material is Emealon 333, a commercially available preparation. The equivalents of this material can be used, as can any fluorinated hydrocarbon (fluorocarbon) that is non-stick, such as Teflon by Dupont or Emeron. Conventional methods (such as dipping, brushing, spraying, and so on) and various solutions for coating the blade may be used, so long as they are suitable for providing a set film, and shrink to the requisite degree, on drying, to reveal a gap along the edge of the electro-surgical tip. The total thickness of the dried set film is preferably in the range of from about 0.0005 to about 0.0015 inches (that is, from 0.5 mils to 1.5 mils).

When the coating dries it shrinks a small amount, for example about 2%, to a sufficient degree that it provides a gap in the coating at the edge of the electro-surgical tip according to the invention. In the prior art, when a primer coat is used, there is no shrinking of the non-stick surface after it is applied, and so no gap forms.

According to the invention, due to the surface preparation, and because of the resulting small amount of shrinkage, for example about 2% shrinkage, the contraction of the non-stick surface exposes the very edge of the surgical blade, along the edge, through a continuous crack in the non-stick coating. The width of the gap will vary, but in preferred embodiments, with a blade, the gap is from about 2 to about 5 microns wide. The size of the gap is sufficient to electrically expose the metal of the tip and to direct an even electrical current through the gap, but not so large as to become susceptible to clogging.

The term "blade" is used here in its broader sense as electrosurgical tips may or may not comprise an actual cutting blade, but employ electrical "blades" of a wide variety of shapes. In embodiments of the present invention with shapes of tips or blades other than a blade with a natural defined edge, such as balls or loops, a raised continuous ridge or raised point is added to the surface of the metal device so that a ridge or point of the underlying metal device is exposed by the small amount of shrinkage or contraction of the non-stick coating. The term "edge" herein is intended to encompass cutting blade edges, defined edges, ridges, raised points, and such other prominent portions that are exposed when a non-stick coating solution is applied and shrinks from an electrosurgical tip on drying to provide a route for electrical discharge according to the invention.

Figure 4:
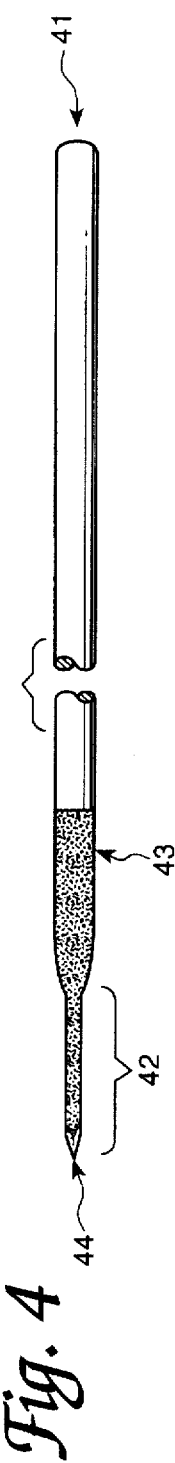
FIG. 4 shows the present invention with a point shape tip portion.

FIG. 4 shows the present invention with a point shape tip portion. Shank 41 is shown attached to coated portion 43 (hash marks), including pointed tip portion 42; with a raised uncoated point 44.

The embodiments illustrated and discussed in this specification are intended only to teach those skilled in the art the best way known to the inventors to make and use the invention. Nothing in this specification should be considered as limiting the scope of the present invention. Modifications and variations of the above-described embodiments of the invention are possible without departing from the invention, as appreciated by those skilled in the art in light of the above teachings. It is therefore to be understood that, within the scope of the claims and their equivalents, the invention may be practiced otherwise than as specifically described.

What is claimed is:

1. A method comprising:
   (a) developing a non-shiny surface on a metal electro-surgical tip having a blade with an edge, where the non-shiny surface is developed by airblasting with tiny particles,
   (b) heating the tip to oxidize the metal,
   (c) dipping the tip into a liquid preparation of a non-stick fluorinated hydrocarbon coating selected to contract a predetermined amount on drying, and
   (d) allowing the coating to dry and to contract a sufficient degree to expose the edge of the blade with a gap from about 2 to about 5 microns wide, and sufficient to direct the flow of an electric current through the exposed area at the edge of the blade.

2. A method comprising:
   (a) obtaining a metal electro-surgical tip having an edge,
   (b) applying to the tip a liquid preparation of a non-stick coating, and
   (d) allowing the coating to dry and to contract a sufficient degree to electrically expose a portion of the dipped surface of the metal tip at the edge.

3. The method of claim 2, further comprising roughening the electro-surgical tip to provide a non-shiny surface, and heating the tip to oxidize the metal, before applying the coating.

4. The method of claim 3, where the non-shiny surface is developed by airblasting or rough tumbling with cutting compound.

5. The method of claim 3, wherein the heating is to about 800° F. in an air environment at about one atmosphere pressure for about 30 minutes.

6. The method of claim 2, where the tip has a defined edge and a shape selected from the group of shapes consisting of a blade, loop, ball, cautery, surgical pencil, and pointed tip.

7. The method of claim 2, where the coating is selected from the group consisting of Emealon 333, Teflon, Emeron, and non-stick fluorocarbons.

8. The method of claim 2, where the tip is an electro-surgical blade, and the exposed area is the edge of the blade and is about 2 to about 5 microns wide.

9. The method of claim 2, where the coating is from about 0.5 to about 1.5 mils thick.

* * * * *